(12) United States Patent
Senetar et al.

(10) Patent No.: US 11,078,435 B2
(45) Date of Patent: Aug. 3, 2021

(54) PROCESS FOR CRACKING AN OLEFINIC FEED COMPRISING DIOLEFINS AND MONOOLEFINS

(71) Applicant: UOP LLC, Des Plaines, IL (US)

(72) Inventors: John J. Senetar, Naperville, IL (US); Christopher R. Schindlbeck, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 143 days.

(21) Appl. No.: 16/403,592

(22) Filed: May 5, 2019

(65) Prior Publication Data

US 2020/0347310 A1    Nov. 5, 2020

(51) Int. Cl.
C10G 69/08     (2006.01)
C07C 5/05      (2006.01)
C07C 4/06      (2006.01)

(52) U.S. Cl.
CPC .............. *C10G 69/08* (2013.01); *C07C 4/06* (2013.01); *C07C 5/05* (2013.01); *C10G 2300/1088* (2013.01); *C10G 2400/20* (2013.01)

(58) Field of Classification Search
CPC .............. C10G 69/08; C10G 2400/20; C10G 2300/1088; C07C 5/05; C07C 4/06
See application file for complete search history.

(56) References Cited

U.S. PATENT DOCUMENTS

| | | |
|---|---|---|
| 7,268,265 B1 | 9/2007 | Stewart et al. |
| 8,829,259 B2 | 9/2014 | Bozzano et al. |
| 2007/0129588 A1 | 6/2007 | Kalnes et al. |
| 2010/0331590 A1 | 12/2010 | Majumder |
| 2016/0347688 A1 | 1/2016 | Linde |

OTHER PUBLICATIONS

PCT, "PCT/US2020/031261 Search Report".
PCT ISA, "PCT Written Opinion PCT/US2020/031261".
Beskov, "General Industrial Chemistry and Basics of Industrial Ecology: Textbook for Universities, Moscow Ohemistry", 1999, pp. 182-184.

*Primary Examiner* — Thuan D Dang
(74) *Attorney, Agent, or Firm* — Paschall & Associates, LLC; James C. Paschall (57) ABSTRACT

A process for cracking an olefinic feed comprising diolefins and monoolefins is provided. The process comprises selectively hydrogenating the olefinic feed in a hydrogenation reactor to convert the diolefins to monoolefins to provide a hydrogenated effluent stream. The hydrogenated effluent stream is vaporized to provide a vaporized hydrogenated effluent stream. The vaporized hydrogenated effluent stream is passed to an olefin cracking reactor to provide a cracked olefin stream comprising $C_2$ and $C_3$ olefins. The cracked olefin stream is passed to a recycle column to provide one of an overhead vapor stream comprising $C_{5-}$ hydrocarbons or a side draw vapor stream comprising $C_{6+}$. At least a portion of the overhead vapor stream or the side draw vapor stream is recycled to the olefin cracking reactor.

18 Claims, 3 Drawing Sheets

PROCESS FOR CRACKING AN OLEFINIC FEED COMPRISING DIOLEFINS AND MONOOLEFINS

FIELD

The field relates to processes for cracking an olefinic feed comprising diolefins and monoolefins. More particularly, the technical field relates to cracking an olefinic feed comprising diolefins and monoolefins to produce $C_2$ and $C_3$ olefins.

BACKGROUND

Light olefins serve as feed materials for the production of numerous chemicals. Light olefins, primarily ethylene and propylene, serve as feeds for plastics production and for the production of petrochemicals. Conventionally, light olefins are being produced through the process of steam or catalytic cracking. However, due to high demand of the light olefins compounded with the limitations associated with the conventional processes, researchers are striving to find an alternate process for the production of light olefins.

Traditionally, light olefins are produced through Olefin Cracking Process (OCP) of heavy hydrocarbons such as derived from petroleum sources wherein a heavy feedstock like vacuum gas oil, reduced crude, etc. of relatively high boiling point is used.

Conventional Olefin Cracking Processes (OCP) have several limitations that prevent operation at optimal conditions to maximize light olefin yield. These limitations arise from the inability to achieve and maintain the desired Weight Hourly Space Velocity (WHSV) in reactor. Lower than desired WHSV results in over-cracking of a feed and subsequent generation of excessive heavies. There are various conditions under which the conventional olefin cracking processes lead to low WHSV. Such conditions may include, inter alia, decreased fresh feed rate, and inability to maintain appropriate recycle to the reactor due to step change in operations when switching OCP reactors for regeneration. Switching the OCP reactors may lead to loss of adequate hydrocarbons for recycle. Cumulative effect of such conditions may lead to a light olefin yield which is lower than desired whereas the yield of heavies may be significantly higher.

Accordingly, it is desirable to provide new processes for providing cost benefits in terms of lower capital and operational expenditures. Further, there is a need for an alternative approach for an improved olefin cracking process to improve recovery of lower hydrocarbons to meet the globally rising demand. Also, there is a need for an alternative approach for cracking an olefinic feed to improve the conversion of olefinic feed to lower hydrocarbons with improved WHSV to reduce over-cracking of the feed and subsequent generation of excessive heavies. Other desirable features and characteristics of the present subject matter will become apparent from the subsequent detailed description of the subject matter and the appended claims, taken in conjunction with the accompanying drawings and this background of the subject matter.

BRIEF SUMMARY

In one embodiment, a process for cracking an olefinic feed comprising diolefins and monoolefins comprises selectively hydrogenating the olefinic feed in a hydrogenation reactor to convert the diolefins to monoolefins and provide a hydrogenated effluent stream. The hydrogenated effluent stream is vaporized in a vaporizer to provide a vaporized hydrogenated effluent stream. The vaporized hydrogenated effluent stream is passed to an olefin cracking reactor to crack at least a portion of the olefins present therein and provide a cracked olefin stream comprising $C_2$ and $C_3$ olefins. The cracked olefin stream is passed to a recycle column to provide one of an overhead vapor stream comprising $C_{5-}$ hydrocarbons or a side draw vapor stream comprising $C_{6+}$ hydrocarbons. From the recycle column, at least a portion of the overhead vapor stream or the side draw vapor stream is recycled to the olefin cracking reactor.

In the current process, the overhead vapor stream comprising $C_{5-}$ hydrocarbons or the side draw vapor stream comprising $C_{6+}$ hydrocarbons may be recycled to the olefin cracking reactor to ensure adequate WHSV in the olefin cracking reactor 150 during the olefin cracking process regardless of turndown and switching of reactors. The current process, by recycling the overhead vapor stream comprising $C_{5-}$ hydrocarbons or the side draw vapor stream comprising $C_{6+}$ hydrocarbons to the olefin cracking reactor, decreases the yield of heavy hydrocarbons and/or heavies that may generate and ensures a desired yield of light olefins. Further, recycling the overhead vapor stream comprising $C_{5-}$ hydrocarbons or the side draw vapor stream comprising $C_{6+}$ hydrocarbons to the olefin cracking reactor also helps in maintaining the flow rate through the olefin cracking reactor at turndown and when any upset occurs while switching the reactor.

These and other features, aspects, and advantages of the present invention will become better understood upon consideration of the following detailed description, drawings and appended claims.

BRIEF DESCRIPTION OF THE DRAWING

The various embodiments will hereinafter be described in conjunction with the following FIGURES, wherein like numerals denote like elements.

DETAILED DESCRIPTION

Various embodiments herein relate to processes for cracking an olefinic feed comprising diolefins and monoolefins. As used herein, the term "column" means a distillation column or columns for separating one or more components of different volatilities. Unless otherwise indicated, each column includes a condenser on an overhead of the column to condense the overhead vapor and reflux a portion of an overhead stream back to the top of the column. Also included is a reboiler at a bottom of the column to vaporize and send a portion of a bottom stream back to the bottom of the column to supply fractionation energy. Feeds to the columns may be preheated. The top pressure is the pressure of the overhead vapor at the outlet of the column. The bottom temperature is the liquid bottom outlet temperature.

Overhead lines and bottom lines refer to the net lines from the column downstream of the reflux or reboil to the column. Alternatively, a stripping stream may be used for heat input at the bottom of the column.

As used herein, the term "stream" can include various hydrocarbon molecules and other substances.

As used herein, the term "overhead stream" can mean a stream withdrawn in a line extending from or near a top of a vessel, such as a column.

As used herein, the term "bottoms stream" can mean a stream withdrawn in a line extending from or near a bottom of a vessel, such as a column.

As used herein, the term "passing" includes "feeding" and "charging" and means that the material passes from a conduit or vessel to an object.

The term "$C_{x-}$" wherein "x" is an integer means a hydrocarbon stream with hydrocarbons have x and/or less carbon atoms and preferably x and less carbon atoms.

The term "$C_{x+}$" wherein "x" is an integer means a hydrocarbon stream with hydrocarbons have x and/or more carbon atoms and preferably x and more carbon atoms.

The term "directly" means that flow from the upstream component enters the downstream component without undergoing a compositional change due to physical fractionation or chemical conversion.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator. The separator may be operated at higher pressure than the flash drum.

As used herein, the term "combined feed ratio" means a ratio of the sum of a fresh feed rate and a recycle feed rate to the enumerated component to the fresh feed rate to the enumerated component. If "X" is the fresh feed rate to the enumerated component and "Y" is the recycle feed rate to the enumerated component, the "combined feed ratio" will be defined as (X+Y)/X.

As used herein, the term "portion" means an amount or part taken or separated from a main stream without any change in the composition as compared to the main stream. Further, it also includes splitting the taken or separated portion into multiple portions where each portion retains the same composition as compared to the main stream.

As used herein, the term "heavies" means heavy hydrocarbons, such as $C_{9+}$ hydrocarbons. It also includes unconverted oil comprising $C_{9+}$ hydrocarbons produced in the reactor.

The following detailed description is merely exemplary in nature and is not intended to limit the various embodiments or the application and uses thereof. The figures have been simplified by the deletion of a large number of apparatuses customarily employed in a process of this nature, such as vessel internals, temperature and pressure controls systems, flow control valves, recycle pumps, etc. which are not specifically required to illustrate the performance of the invention. Furthermore, the illustration of the process of this invention in the embodiment of a specific drawing is not intended to limit the invention to specific embodiments set out herein.

Figure 1:
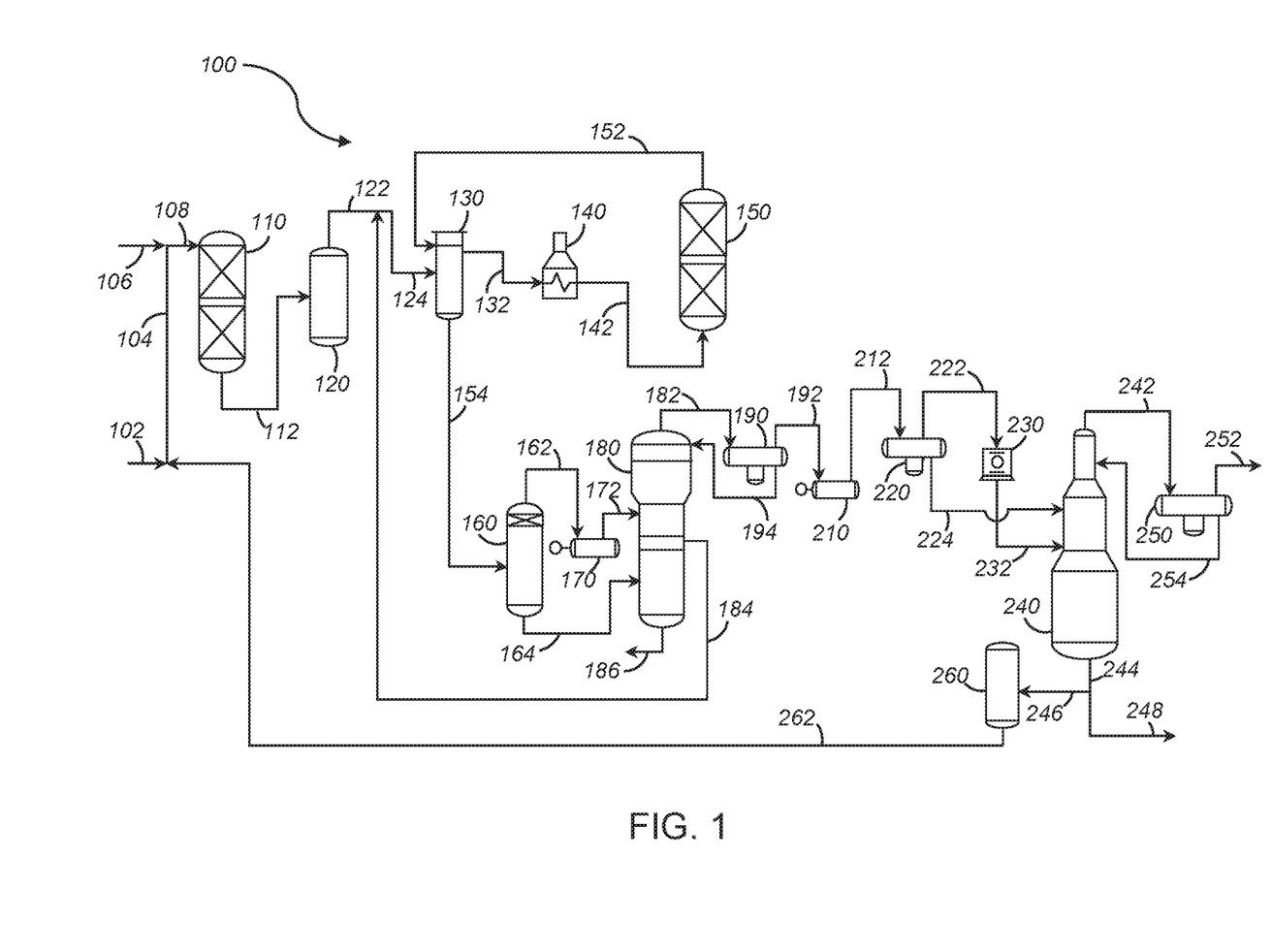
FIG. 1 is a schematic diagram of a process and an apparatus for cracking an olefinic feed comprising diolefins and monoolefins in accordance with an exemplary embodiment.

A process for cracking an olefinic feed comprising diolefins and monoolefins is addressed with reference to a process and apparatus 100 according to an embodiment as shown in FIG. 1. Referring to FIG. 1, the process and apparatus 100 comprise a hydrogenation reactor 110, a vaporizer 120, a combined feed heat exchanger 130, a charge heater 140, an olefin cracking reactor 150, a first separator 160, a recycle column 180, a second separator 220, compressors 170, 210, and 230, and a depropanizer column 240. In FIG. 1, an olefinic feed comprising diolefins and monoolefins in line 102 is provided. A recycle liquid stream in line 262 may be combined with the olefinic feed 102 to form a first combined stream in line 104. The first combined stream 104 may be passed to the hydrogenation reactor 110. A hydrogen gas stream in line 106 may also join the first combined stream 104 to form a second combined stream in line 108. The second combined stream 108 may be passed to the hydrogenation reactor 110. In another embodiment, both the first combined stream 104 and the hydrogen gas stream 106 may be passed separately to the hydrogenation reactor 110. In yet another embodiment, the olefinic feed 102, the recycle liquid stream 262, and the hydrogen gas stream 106 may be passed separately to the hydrogenation reactor 110.

The olefinic feed to the hydrogenation reactor 110 in accordance with the present disclosure comprises $C_4$ and higher olefins. In an embodiment, the olefinic feed to the hydrogenation reactor 110 may comprise $C_4$ to $C_7$ olefins. The olefinic feed may be obtained from a fluid catalytic cracking (FCC) product stream, a $C_{4+}$ stream of a steam cracker furnace, a methanol-to-olefin (MTO) process, or the olefinic feed may be a VGO stream. To maximize the conversion of olefinic feed to $C_2$ and $C_3$ olefins, the amount of diolefins and/or acetylenes present in the olefinic feed should be reduced. To reduce the concentration of diolefins and/or acetylenes, second combined stream 108 comprising both first combined stream 104 and hydrogen gas stream 106 may be passed to hydrogenation reactor 110. In hydrogenation reactor 110, the olefinic feed 102 and the recycle liquid stream 262 are selectively hydrogenated in the presence of a hydrogenation catalyst to convert the diolefins and/or acetylenes present therein to monoolefins without significant monoolefins saturation present in the olefinic feed 102 to provide a hydrogenated effluent stream in line 112. The hydrogenated effluent stream 112 comprises substantially reduced amount of diolefins compared to the olefinic feed 102. In an embodiment, the amount of diolefins present in the hydrogenated effluent stream 112 is lower than 100 ppm.

The hydrogenation reactor 110 may contain one or more beds of the hydrogenation catalyst. In the hydrogenation reactor 110, the olefinic feed 102 and the recycle liquid stream 262 are selectively hydrogenated in the presence of the hydrogenation catalyst. In FIG. 1, the hydrogenation reactor 110 comprises two beds of the hydrogenation catalyst. Although not shown in FIG. 1, the second combined stream 108 may be separated into a plurality of streams. Therefore, a stream from the plurality of streams may be sent to a top hydrogenation catalyst bed and remaining streams may be passed to downstream hydrogenation catalyst beds in the hydrogenation reactor 110 as a quench streams for an effluent stream exiting an upstream hydrogenation catalyst bed. Each hydrogenation catalyst bed may comprise similar or different hydrogenation catalyst as compared to the other beds of the hydrogenation reactor 110.

Any suitable hydrogenation catalyst may be used in the hydrogenation reactor 110 for selective hydrogenation of the olefinic feed 102. The hydrogenation catalysts may comprise a platinum group component supported on a porous carrier material. The carrier material may be a refractory inorganic oxide such as gamma-alumina. The platinum group component may be chosen from the group consisting of platinum, palladium, rhodium, ruthenium, osmium, and iridium. The hydrogenation catalysts may also comprise an alkali or an alkaline earth component. The alkali or alkaline earth component may be selected from the group consisting of the alkali metals-cesium, rubidium, potassium, sodium, and lithium; and the alkaline earth metals—calcium, strontium, barium, and magnesium. Further, the hydrogenation catalysts may comprise one or more metallic components from the group of nickel, molybdenum, cobalt, tungsten, and mixtures thereof.

The hydrogenated effluent stream 112 may be passed to the vaporizer 120 to form a vaporized hydrogenated effluent stream in line 122. The vaporized hydrogenated effluent stream 122 may be passed to the olefin cracking reactor 150. In the olefin cracking reactor 150, at least a portion of the olefins present in the vaporized hydrogenated effluent stream 122 are cracked to provide a cracked olefin stream comprising $C_2$ and $C_3$ olefins in line 152. A recycle vapor stream in line 184 may also be combined with the vaporized hydrogenated effluent stream 122 to form a combined vaporized stream in line 124. The combined vaporized stream 124 may be passed to the olefin cracking reactor 150. As shown, the combined vaporized stream 124 may be heat exchanged with the cracked olefin stream 152 in the combined feed heat exchanger 130 to form a heat-exchanged combined vaporized stream in line 132. In an exemplary embodiment, the vaporized hydrogenated effluent stream 122 may be heated to a predetermined temperature prior to passing the vaporized hydrogenated effluent stream 122 to the olefin cracking reactor 150. The heat-exchanged combined vaporized stream 132 may be passed to the charge heater 140 prior to the olefin cracking reactor 150 to heat the heat-exchanged combined vaporized stream 132 to the predetermined temperature. Thereby, ensuring a vaporized form of the heat-exchanged combined vaporized stream 132. In the charge heater 140, the heat-exchanged combined vaporized stream 132 is heated to the predetermined temperature to form a further vaporized stream in line 142 which is passed to the olefin cracking reactor 150. In an alternate scheme, the vaporized hydrogenated effluent stream 122 and the recycle vapor stream 184 may be passed to the combined feed heat exchanger 130 and thereafter to the charge heater 140 separately.

The olefin cracking reactor 150 may contain one or more beds of the cracking catalyst. In the olefin cracking reactor 150, at least a portion of the olefins present therein are cracked in the presence of the cracking catalyst to provide the cracked olefin stream comprising $C_2$ and $C_3$ olefins in line 152. Suitable cracking conditions may be maintained in the olefin cracking reactor 15 for higher olefins to produce $C_2$ and $C_3$ olefins. Suitable operating conditions of the olefin cracking reactor 150 may comprise an inlet temperature from about 400° C. to about 600° C., or from about 520° C. to about 600° C., and an olefin partial pressure from about 10 kPa absolute (1.5 psia) to about 202 kPa absolute (29 psia), or from 50 kPa absolute (7.0 psia) to about 152 kPa absolute (22 psia). Although not shown in FIG. 1, the olefin cracking reactor 150 may comprise a regeneration reactor to regenerate the exhausted catalyst coming from the olefin cracking reactor 150 and providing a regenerated catalyst back to the olefin cracking reactor 150.

Cracking catalyst suitable for olefin cracking process may comprise a crystalline silicate of the MFI family which may be a zeolite, a silicalite or any other silicate in that family or the MEL family which may be a zeolite or any other silicate in that family. Examples of MFI silicates may include ZSM-5 and silicalite. Further, the MEL zeolite may include ZSM-11, Boralite D, and silicalite-2. The cracking catalyst may be mixed with a binder, and shaped to a desired shape, e.g. extruded pellets. The binder may be an inorganic material selected from clays, silica, metal oxides such as $ZrO_2$ and/or metals, or gels including mixtures of silica and metal oxides.

The olefin cracking reactor 150 may be adaptable to contain one or more beds of the cracking catalyst to provide the cracked olefin stream comprising $C_2$ and $C_3$ olefins in line 152. Each bed may comprise a similar or a different cracking catalyst compared to the other beds of the olefin cracking reactor 150.

The cracked olefin stream comprising $C_2$ and $C_3$ olefins in line 152 may be passed to the combined feed heat exchanger 130 to heat up the combined vaporized stream 124. Thereafter, a heat-exchanged cracked olefin stream in line 154 may be passed to the recycle column 180. In an exemplary embodiment, the heat-exchanged cracked olefin stream 154 may be passed to the recycle column 180 via the first separator 160 to provide an overhead vapor stream comprising $C_{5-}$ hydrocarbons in line 182 and a side draw vapor stream comprising $C_{6+}$ hydrocarbons in line 184. As shown, the heat-exchanged cracked olefin stream 154 may be passed to the first separator 160 to provide a vapor stream in line 162 and a liquid stream in line 164. The first separator 160 may be operated at any suitable temperature to separate the heat-exchanged cracked olefin stream 154 into the vapor stream 162 and the liquid stream 164. The first separator 160 may be operated at a slightly lower pressure than the olefin cracking reactor 150 accounting for pressure drop of intervening equipment. Although not shown, the first separator 160 may have a corresponding flash drum and the liquid stream 164 may be let down in pressure and flashed in the flash drum. In an alternate scheme, the heat-exchanged cracked olefin stream 154 may be further cooled and passed to the first separator 160 to provide the vapor stream 162 and the liquid stream 164.

The present process also provides a multi-stage compression system to facilitate the separation of $C_2$ and $C_3$ olefins from the heat-exchanged cracked olefin stream 154. In an exemplary embodiment as shown in FIG. 1, the multi-stage compression system of the present disclosure comprises three compression stage a first stage compressor 170, a second stage compressor 210, and a third stage compressor 230.

As shown, the vapor stream 162 may be passed to the recycle column 180 via the first stage compressor 170. In the first stage compressor 170, the vapor stream 162 may be compressed to form a compressed cracked olefin stream in line 172. At least a portion the compressed cracked olefin stream 172 may be passed to the recycle column 180. The liquid stream 164 may also be passed to the recycle column 180. In the recycle column 180, the compressed cracked olefin stream 172 and the liquid stream 164 may be separated in to the overhead vapor stream comprising $C_{5-}$ hydrocarbons in line 182, and the side draw vapor stream comprising $C_{6+}$ hydrocarbons in line 184. A recycle column bottoms stream in line 186 may also be obtained. The side draw vapor stream comprising $C_{6+}$ hydrocarbons in line 184 may be recycled to the olefin cracking reactor 150.

In an exemplary embodiment as shown in FIG. 1, the side draw vapor stream comprising $C_{6+}$ hydrocarbons in line 184 is recycled to the olefin cracking reactor 150. In another exemplary embodiment, the side draw vapor stream is a first vapor stream comprising $C_{6+}$ hydrocarbons. Accordingly, the side draw vapor stream or the first vapor stream comprising $C_{6+}$ hydrocarbons in line 184 may be combined with the vaporized hydrogenated effluent stream 122 to form the combined vaporized stream 124. The combined vaporized stream 124 may be passed to the olefin cracking reactor 150.

In another exemplary embodiment, the side draw vapor stream comprising $C_{6+}$ hydrocarbons in line 184 may be passed to the vaporizer 120 along with the hydrogenated effluent stream 112 for recycling to the olefin cracking reactor 150. Further, at least a portion of the overhead vapor stream comprising $C_{5-}$ hydrocarbons in line 182 may be passed to the depropanizer column 240 to provide $C_2$ and $C_3$ olefins in line 252.

In yet another exemplary embodiment, the overhead vapor stream 182 is a second vapor stream comprising $C_{5-}$ hydrocarbons. Accordingly, the overhead vapor stream 182 or the second vapor stream comprising $C_{5-}$ hydrocarbons in line 182 may be passed to the depropanizer column 240. As shown, the overhead vapor stream comprising $C_{5-}$ hydrocarbons in line 182 may be passed to an overhead receiver 190 of the recycle column 180. From the overhead receiver 190, a liquid reflux stream in line 194 may be passed to the recycle column 180. A vapor stream in line 192 from the overhead receiver 190 may be passed to the second stage compressor 210 to provide a first compressed stream in line 212. The first compressed stream 212 may be passed to the second separator 220 to separate the first compressed stream 212 in to a vaporous stream in line 222 and a first liquid stream in line 224. The vaporous stream 222 may be compressed in the third stage compressor 230 to provide a second compressed stream in line 232. The second compressed stream 232 and the first liquid stream 224 may be passed to the depropanizer column 240 to separate $C_2$ and $C_3$ olefins therefrom.

In the depropanizer column 240, the second compressed stream 232 and the first liquid stream 224 are fractionated to provide an overhead vapor stream comprising $C_{3-}$ olefins in line 242. A bottoms liquid stream in line 244 may be separated from the depropanizer column 240. In an exemplary embodiment, the bottoms liquid stream 244 comprises $C_{4+}$ hydrocarbons. The first liquid stream 224 may be passed at a point higher than the point at which the second compressed stream 232 may be passed in to the depropanizer column 240 to facilitate the separation of $C_{3-}$ olefins. The overhead vapor stream comprising $C_{3-}$ olefins in line 242 may be passed to an overhead receiver 250 of the depropanizer column 240 wherein a liquid reflux stream in line 254 may be passed to the depropanizer column 240. From the overhead receiver 250, a vapor stream comprising $C_2$ and $C_3$ olefins in line 252 may be withdrawn as a product stream. At least a portion of the bottoms liquid stream in line 246 may be recycled back to the hydrogenation reactor 110. Further, a remaining portion of the bottoms liquid stream in line 248 may be removed as a purge stream from the process. In another exemplary embodiment, the bottoms liquid stream 244 comprises $C_{6+}$ hydrocarbons. The at least portion of the bottoms stream in line 246 may be recycled to the hydrogenation reactor 110 at a combined feed ratio from about 1:1 to about 5:1. As shown, the at least portion of the bottoms liquid stream in line 246 may be passed to a surge drum 260. From the surge drum 260, the bottoms liquid stream in line 262 may be recycled as the recycle liquid stream in line 262 to the hydrogenation reactor 110 as described herein above. Alternatively, the at least portion of bottoms liquid stream in line 246 may be passed directly to the hydrogenation reactor 110.

Applicants have found that in order to reduce overcracking of olefins and subsequent generation of heavies, a vapor recycle stream can be maintained. The vapor recycle stream ensures adequate WHSV in the olefin cracking reactor 150 during the olefin cracking process regardless of turndown and switching of the olefin cracking reactor 150 in case for regeneration of the catalyst. Accordingly, the side draw vapor stream comprising $C_{6+}$ hydrocarbons in line 184 is withdrawn from the recycle column 180 as the recycle stream. The side draw vapor stream 184 needs to be depleted of $C_{3-}$ olefins so as light olefins are not recycled back to the process. Recycling light olefins back to the process reduces the amount of light olefins available for the final product stream. Thus, reduces the light olefins yield of the olefin cracking process. Therefore, the side draw vapor stream 184 comprises $C_{6+}$ olefins to maintain the $C_2$ and $C_3$ olefins yield. The side draw vapor stream 184 comprising $C_{6+}$ olefins is passed to the olefin cracking reactor 150 for further cracking along with the vaporized hydrogenated effluent stream 122. Since, WHSV of the olefin cracking reactor 150 is independent of the olefin cracking reactor's bottom flow and fresh feed rate, the side draw vapor stream 184 also helps in maintaining the flow rate through the olefin cracking reactor 150 at turndown and when any upset occurs while switching the reactors e.g. decreased feed rate to the olefin cracking reactor 150 or inability to maintain appropriate recycle due to step change in operations when switching the reactors for regeneration.

The side draw vapor stream comprising $C_{6+}$ hydrocarbons in line 184 may be withdrawn from a point below a feed point where the compressed cracked olefin stream 172 is introduced in to the recycle column 180. Thereby, the current process ensures that the side draw vapor stream 184 is depleted of $C_{3-}$ olefins and comprises $C_{6+}$ hydrocarbons for recycling to maintain the yield of $C_2$ and $C_3$ olefins of the olefin cracking process. If the side draw vapor stream in line 184 is withdrawn from a point above the feed point of the compressed cracked olefin stream 172 in the recycle column 180, then a substantial amounts of $C_2$ and $C_3$ olefins would be recycled to the olefin cracking reactor 150. Recycling light olefins back to the process reduces the amount of light olefins available for the final product stream. This will reduce the $C_2$ and $C_3$ olefins yield of the olefin cracking process.

The side draw vapor stream comprising $C_{6+}$ hydrocarbons in line 184 of the current process may be passed directly to the olefin cracking reactor 150 or recycle at or with any suitable stream at a point upstream of the olefin cracking reactor 150. Further, the side draw vapor stream comprising $C_{6+}$ hydrocarbons of the present scheme is withdrawn from the recycle column 180 in line 184 and not from the depropanizer column 240 located downstream of the recycle column 180. Applicants found that when the side draw vapor stream 184 is withdrawn from the depropanizer column 240, a substantial amount of $C_2$ and $C_3$ olefins may be recycled back to the olefin cracking reactor 150 which reduces the desired yield of $C_2$ and $C_3$ olefins. Withdrawing the side draw vapor stream from the depropanizer column 240 cannot maintain the required WHSV in the olefin cracking reactor 150 during the olefin cracking process while turndown and switching of the olefin cracking reactor 150 in case for regeneration of the catalyst. The present process provides the side draw vapor stream comprising $C_{6+}$ hydrocarbons in line 184 from the recycle column 180 to maintain the required WHSV in the olefin cracking reactor 150 and the yield of $C_2$ and $C_3$ olefins from the olefin cracking process.

The current process, by recycling the side draw vapor stream comprising $C_{6+}$ hydrocarbons in line 184 from the recycle column 180 to the olefin cracking reactor 150, increases the WHSV of the olefin cracking reactor 150. Recycling the side draw vapor stream comprising $C_{6+}$ hydrocarbons to the olefin cracking reactor 150 boosts the flow through the olefin cracking reactor 150 to favor light olefins yield. Also, recycling the side draw vapor stream comprising $C_{6+}$ hydrocarbons reduces heavies formation in the olefin cracking reactor 150 by preventing the overcracking of the feed in the olefin cracking reactor 150. By recycling the side draw vapor stream comprising $C_{6+}$ hydrocarbons to the olefin cracking reactor 150, the current process dilutes the olefinic concentration of the feed to an extent to impede oligomerization e.g. an olefin concentration of 50% or below. Accordingly, the present flow scheme may process a feed with high olefinic concentration greater than 90% which are prone to oligomerization under similar operating conditions.

Figure 2:
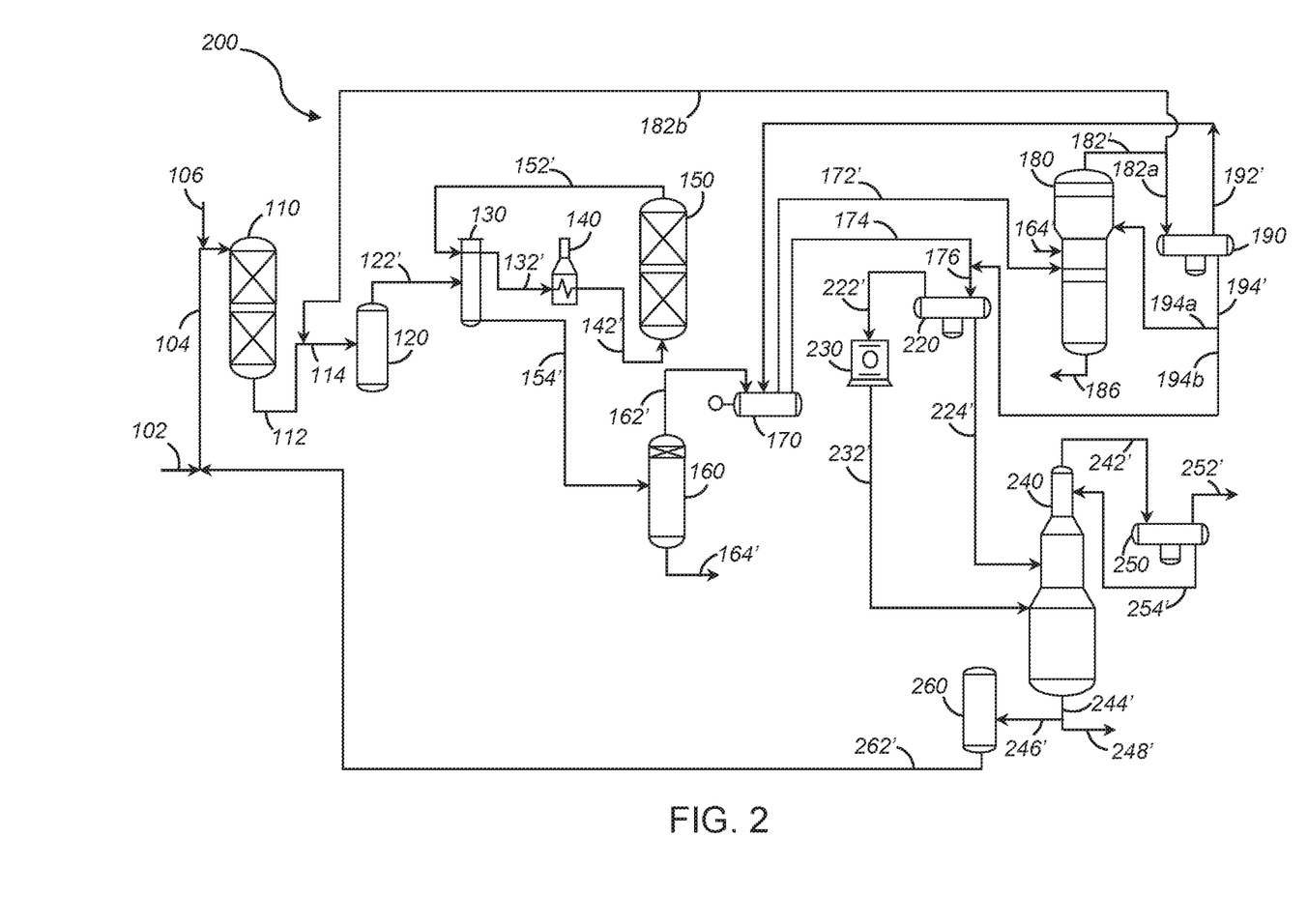
FIG. 2 is a schematic diagram of a process and an apparatus for cracking an olefinic feed comprising diolefins and monoolefins in accordance with another exemplary embodiment.

Turning now to FIG. 2, another exemplary embodiment of the process for cracking an olefinic feed comprising diolefins and monoolefins is addressed with reference to a process and apparatus 200. Elements of FIG. 2 may have the same configuration as in FIG. 1 and bear the same respective reference number and have similar operating conditions. Elements in FIG. 2 that correspond to elements in FIG. 1 but have a different configuration bear the same reference numeral as in FIG. 1 but are marked with a prime symbol (').

As shown in FIG. 2, the hydrogenated effluent stream 112 may be combined with an overhead vapor stream comprising $C_{5-}$ hydrocarbons in line 182b to form a combined stream in line 114. The combined stream 114 may be passed to the vaporizer 120 to form the vaporized hydrogenated effluent stream in line 122'. In an alternate scheme, the hydrogenated effluent stream 112 may be first passed to the vaporizer 120 to form a vaporized hydrogenated effluent stream. And, the overhead vapor stream comprising $C_{5-}$ hydrocarbons in line 182b may be combined with the vaporized hydrogenated effluent stream to form a combined vaporized stream in line 122'. The vaporized hydrogenated effluent stream 122' or the combined vaporized stream 122' may be passed to the olefin cracking reactor 150 to crack at least a portion of the olefins present therein to provide a cracked olefin stream comprising $C_2$ and $C_3$ olefins in line 152'. In an alternate scheme, both the hydrogenated effluent stream 112 and the overhead vapor stream comprising $C_{5-}$ hydrocarbons in line 182b may be passed to the vaporizer 120 separately to form the vaporized hydrogenated effluent stream 122'. As shown, the vaporized hydrogenated effluent stream 122' may be heat exchanged with the cracked olefin stream 152' in the combined feed heat exchanger 130 to further heat up the vaporized hydrogenated effluent stream. In an exemplary embodiment, the vaporized hydrogenated effluent stream 122' may be heated to a predetermined temperature prior to passing the vaporized hydrogenated effluent stream 122' to the olefin cracking reactor 150. A heat-exchanged vaporized hydrogenated effluent stream in line 132' may be passed to the charge heater 140 prior to the olefin cracking reactor 150. In the charge heater 140, the heat-exchanged vaporized hydrogenated effluent stream 132' is heated to the predetermined temperature to provide a further vaporized stream in line 142' which is passed to the olefin cracking reactor 150. In an alternate scheme, the vaporized hydrogenated effluent stream 122' and the overhead vapor stream comprising $C_{5-}$ hydrocarbons in line 182b may be passed to the combined feed heat exchanger 130 and further to the charge heater 140 separately.

The cracked olefin stream comprising $C_2$ and $C_3$ olefins in line 152' may be passed to the combined feed heat exchanger 130 to heat up the combined vaporized stream 122'. Thereafter, a heat-exchanged cracked olefin stream in line 154' may be passed the recycle column 180. In an exemplary embodiment, the heat-exchanged cracked olefin stream 154' may be passed to the recycle column 180 via the first separator 160 to provide an overhead vapor stream comprising $C_{5-}$ hydrocarbons in line 182' and a bottoms liquid stream comprising $C_{6+}$ hydrocarbons in line 186'. The heat-exchanged cracked olefin stream 154' may be passed to the first separator 160 to separate the heat-exchanged cracked olefin stream 154' in to a vapor stream in line 162' and a liquid stream in line 164'. In an alternate scheme, the heat-exchanged cracked olefin stream 154' may be further cooled and passed to the first separator 160 to provide the vapor stream 162' and the liquid stream 164'. As shown, the vapor stream 162' may be passed to the recycle column 180 via the first stage compressor 170. In the first stage compressor 170, the vapor stream 162' may be compressed to form a compressed cracked olefin stream. In the first stage compressor 170, an at least a portion of overhead receiver vapor stream in line 192' from the overhead receiver 190 may also be passed and compressed along with the vapor stream 162' to provide the compressed cracked olefin stream. At least a portion the compressed cracked olefin stream in line 172' may be passed to the recycle column 180. A remaining portion of the compressed cracked olefin stream in line 174 may be passed to the depropanizer column 240 via the second separator 220 to provide $C_2$ and $C_3$ olefins. Alternatively, the vapor stream 162' and the overhead receiver vapor stream 192' may be compressed in the first stage compressor 170 to provide a first compressed cracked olefin stream in line 172' and a second compressed cracked olefin stream in line 174. The first compressed cracked olefin stream 172' may be passed to the recycle column 180 and the second compressed cracked olefin stream 174 may be passed to the depropanizer column 240 via the second separator 220. The liquid stream 164' may also be passed to the recycle column 180. In the recycle column 180, the at least portion of the compressed cracked olefin stream 172' and the liquid stream 164' may be separated in to the overhead vapor stream comprising $C_{5-}$ hydrocarbons in line 182' and the bottoms liquid stream comprising $C_{6+}$ hydrocarbons in line 186'. At least a portion of the overhead vapor stream comprising $C_{5-}$ hydrocarbons in line 182b may be recycled to the olefin cracking reactor 150. A remaining portion of the overhead vapor stream comprising $C_{5-}$ hydrocarbons in line 182a may be passed to the depropanizer column 240 to separate $C_{3-}$ olefins present therein.

As shown, the vapor stream 182', prior to passing the overhead receiver 190 of the recycle column 180, may be separated to provide the at least portion of the overhead vapor stream comprising $C_{5-}$ hydrocarbons in line 182b and the remaining portion of the vapor stream comprising $C_{5-}$ hydrocarbons in line 182a. The at least portion of the overhead vapor stream comprising $C_{5-}$ hydrocarbons in line 182b may be recycled to the olefin cracking reactor 150 at a predetermined temperature. The at least portion of the overhead vapor stream comprising $C_{5-}$ hydrocarbons in line 182b may be combined with the hydrogenated effluent 112 from the hydrogenation reactor 110 to form the combined stream 114. The combined stream 114 may be passed to the vaporizer 120. Alternatively, the at least portion of the overhead vapor stream comprising $C_{5-}$ hydrocarbons in line 182b may be passed to the vaporizer 120 separately. In an exemplary embodiment, the at least portion of the overhead vapor stream comprising $C_{5-}$ hydrocarbons in line 182b may be combined with the hydrogenated effluent stream 112 at a temperature from about 50° C. to about 60° C. The at least portion of the overhead vapor stream comprising $C_{5-}$ hydrocarbons in line 182b may be passed directly to the olefin cracking reactor 150 or recycle at or with any suitable stream at a point upstream of the olefin cracking reactor 150. The remaining portion comprising $C_{5-}$ in line 182a may be passed to the overhead receiver 190 of the recycle column 180 to provide the overhead receiver vapor stream 192' and an overhead receiver liquid stream in line 194'. The overhead receiver vapor stream 192' may be passed to the first stage compressor 170 to compress the overhead receiver vapor stream 192' along with the vapor stream 162'. Accordingly, flow scheme of FIG. 2 compresses the vapor stream 162' and the overhead receiver vapor stream 192' combinedly in the first stage compressor 170. However, the second stage compressor 210 as shown in FIG. 1 may also be used for compressing the vapor stream 162 and the overhead receiver vapor stream 192' separately.

The overhead receiver liquid stream 194' may be separated for further recovery of the hydrocarbons present therein. At least a portion of the overhead receiver liquid stream in line 194b may be passed to the depropanizer column 240 to provide $C_2$ and $C_3$ olefins. And, another portion of the liquid stream in line 194a may be recycled to the recycle column 180 as reflux stream. The at least portion of the liquid stream in line 194b and the remaining portion of the compressed cracked olefin stream in line 174 may be passed to the depropanizer column 240 via the second separator 220 to provide $C_2$ and $C_3$ olefins. As shown, the at least portion of the liquid stream in line 194b may be combined with the remaining portion of the compressed cracked olefin stream in line 174. A combined stream in line 176 may be passed to the second separator 220 to provide a vaporous stream in line 222' and a liquid stream in line 224'. In an alternate scheme, the at least portion of the overhead receiver liquid stream in line 194b and the remaining portion of the compressed cracked olefin stream in line 174 may be passed separately to the second separator 220. The vaporous stream 222' may be compressed in the third stage compressor 230 to provide a compressed vaporous stream in line 232'. The compressed vaporous stream 232' and the liquid stream 224' may be passed to the depropanizer column 240 to separate $C_{3-}$ olefins present therein.

In the depropanizer column 240, the compressed vaporous stream 232' and the liquid stream 224' are fractionated to provide an overhead vapor stream comprising $C_{3-}$ olefins in line 242'. A bottoms liquid stream in line 244' may be separated from the depropanizer column 240. In an exemplary embodiment, the bottoms liquid stream 244' comprises $C_{4+}$ hydrocarbons. The overhead vapor stream comprising $C_3$-olefins in line 242' may be passed to the overhead receiver 250 of the depropanizer column 240 wherein a liquid reflux stream in line 254' may be passed to the depropanizer column 240. From the overhead receiver 250, a vapor stream comprising $C_2$ and $C_3$ olefins in line 252' may be withdrawn as a product stream. At least a portion of the bottoms liquid stream in line 246' may be recycled back to the hydrogenation reactor 110. Further, a remaining portion of the bottoms liquid stream in line 248' may be removed as a purge stream from the process. In another exemplary embodiment, the bottoms liquid stream 244' comprises $C_{6+}$ hydrocarbons. The at least portion of the bottoms stream in line 246' may be recycled to the hydrogenation reactor 110 at a combined feed ratio from about 1:1 to about 5:1. As shown, the at least portion of the bottoms liquid stream in line 246' may be passed to the surge drum 260. From the surge drum 260, the bottoms liquid stream in line 262' may be recycled as the recycle liquid stream in line 262' to the hydrogenation reactor 110. Alternatively, the at least portion of the bottoms liquid stream in line 246' may be passed directly to the hydrogenation reactor 110.

During the periods of operation with lower than design feed, e.g. start-up of the olefin cracking process and at turndown operations, the WHSV for the olefin cracking reactor 150 is low. Low WHSV favors side reactions such as the conversion of olefins to heavier aromatic compounds which is not favorable. Under such periods of operation, the amount of $C_{6+}$ hydrocarbons available in the vapor form that can be obtained from the recycle column 180 is not significant for recycling. Such periods of operation necessitate an alternative approach to improve the operating flexibility of the olefin cracking process. To improve an operating flexibility under such periods of operation, applicants have found that at least a portion of the overhead vapor stream comprising $C_{5-}$ hydrocarbons in line 182b and/or the depropanizer column bottoms stream comprising $C_{4+}$ hydrocarbons in line 244' may be recycled to the olefin cracking reactor as described herein above to improve the light olefin yield by allowing for adequate reactor space velocity (WHSV) in the olefin cracking reactor 150. Such a WHSV favors light olefin yield and reduces heavies generation. Reducing heavies generation may also increase the amount of $C_{4+}$ material, particularly $C_4$-$C_6$ hydrocarbons, available for recycle from the depropanizer column bottoms. Accordingly, the process described herein above in FIG. 2, may particularly be suitable for the start-up and at turndown operations of the olefin cracking process.

Applicants have found that passing the overhead vapor stream comprising $C_{5-}$ hydrocarbons in line 182b to the vaporizer 120 minimizes any liquid carry over to the combined feed heat exchanger 130 and further equipment. As shown in FIG. 2, passing the overhead vapor stream comprising $C_{5-}$ hydrocarbons in line 182b at a temperature from about 50° C. to about 60° C. to the vaporizer 120 has multi-pronged benefits. Firstly, it facilitates the vaporization of the hydrogenated effluent stream 112 in the vaporizer 120 by lowering the vapor pressure within the vaporizer 120. Secondly, passing the vapor stream at such temperatures reduces a dew point temperature of the recycle vapor stream thereby minimizing the amount of liquid that can condense in a recycle line when the recycle line is cool and not in use.

Figure 3:
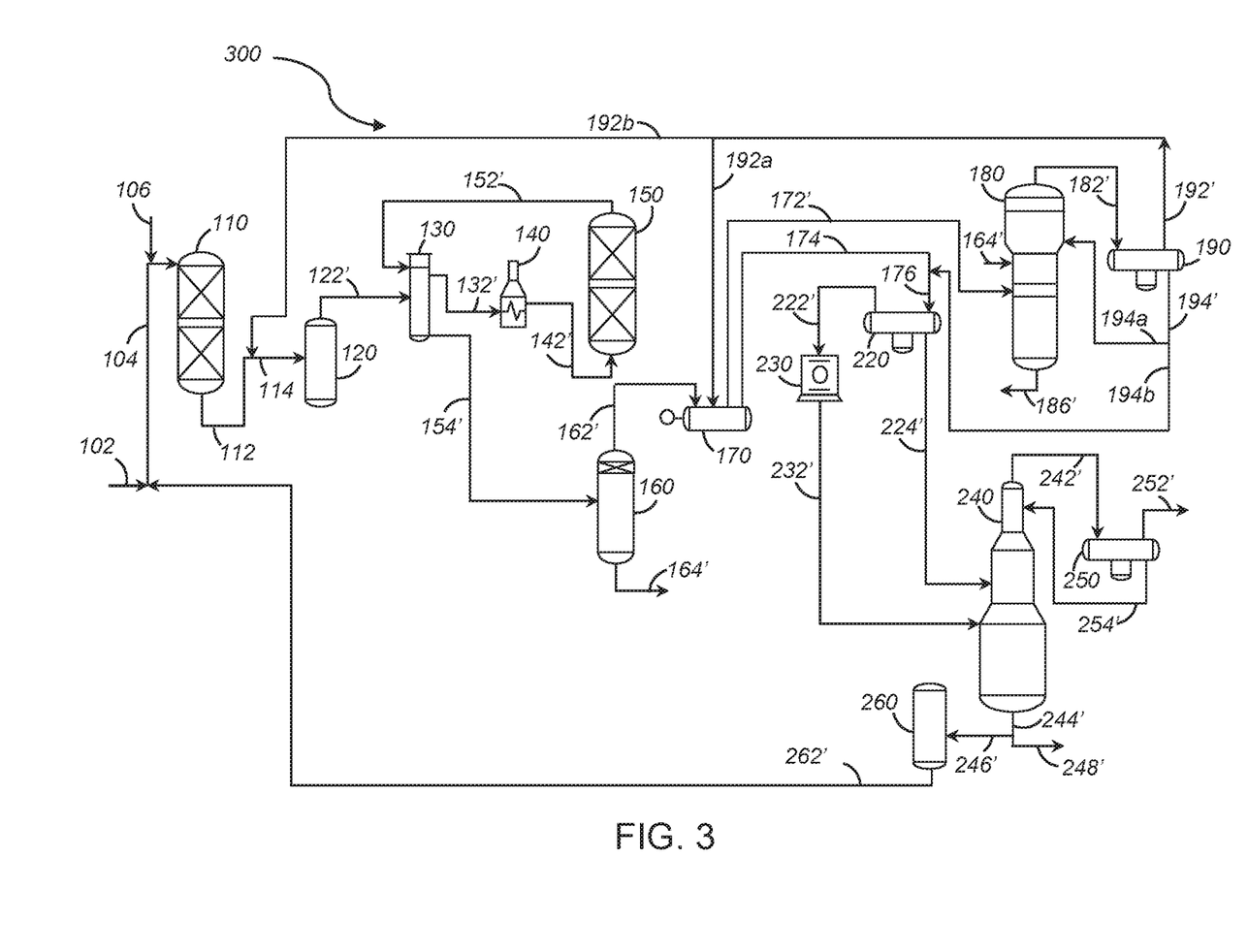
FIG. 3 is a schematic diagram of a process and an apparatus for cracking an olefinic feed comprising diolefins and monoolefins in accordance with yet another exemplary embodiment.

Turning now to FIG. 3, yet another exemplary embodiment of the process for cracking an olefinic feed comprising diolefins and monoolefins is addressed with reference to a process and apparatus 300. Elements of FIG. 3 may have the same configuration as in FIG. 2 and bear the same respective reference number and have similar operating conditions.

As shown in FIG. 3, the hydrogenated effluent stream 112 may be combined with an overhead receiver vapor stream comprising $C_{5-}$ hydrocarbons in line 192b to provide a combined stream in line 114. The combined stream 114 may be passed to the vaporizer 120 to form the vaporized hydrogenated effluent stream 122'. The vaporized hydrogenated effluent stream 122' may be passed to the olefin cracking reactor 150 to crack at least a portion of the olefins present therein to provide a cracked olefin stream comprising $C_2$ and $C_3$ olefins in line 152'. In an alternate scheme, both the hydrogenated effluent stream 112 and the overhead receiver vapor stream comprising $C_{5-}$ hydrocarbons in line 192b may be passed to the vaporizer 120 separately to provide the vaporized hydrogenated effluent stream 122'. As shown, the vaporized hydrogenated effluent stream 122' may be heat exchanged with the cracked olefin stream 152' in the combined feed heat exchanger 130 to further heat up the vaporized hydrogenated effluent stream 122'. In an exemplary embodiment, the vaporized hydrogenated effluent stream 122' may be heated to a predetermined temperature prior to passing the vaporized hydrogenated effluent stream 122' to the olefin cracking reactor 150. Therefore, a heat-exchanged vaporized hydrogenated effluent stream in line 132' may be passed to the charge heater 140 prior to the olefin cracking reactor 150. In the charge heater 140, the vaporized hydrogenated effluent stream 132' is heated to the predetermined temperature to form a further vaporized stream in line 142' which is passed to the olefin cracking reactor 150. In an alternate scheme, the vaporized hydrogenated effluent stream 122' and the overhead receiver vapor stream comprising $C_{5-}$ hydrocarbons in line 192b may be passed to the combined feed heat exchanger 130 and further to the charge heater 140 separately.

The heat-exchanged cracked olefin stream 154' may be passed to the first separator 160. As shown, the vapor stream 162' may be passed to the recycle column 180 via the first stage compressor 170. In the first stage compressor 170, the vapor stream 162' may be compressed to provide the compressed cracked olefin stream. In the first stage compressor 170, a remaining portion of the overhead receiver vapor stream in line 192a from the overhead receiver 190 may also be passed and compressed along with the vapor stream 162' to provide the compressed cracked olefin stream. At least a portion the compressed cracked olefin stream in line 172' may be passed to the recycle column 180. The remaining portion of the compressed cracked olefin stream in line 174 may be passed to the depropanizer column 240 via the second separator 220 to provide $C_2$ and $C_3$ olefins. Alternatively, the vapor stream 162' and the overhead receiver vapor stream 192' may be compressed in the first stage compressor 170 to provide a first compressed cracked olefin stream in line 172' and a second compressed cracked olefin stream in line 174. The first compressed cracked olefin stream 172' may be passed to the recycle column 180 and the second compressed cracked olefin stream 174 may be passed to the depropanizer column 240 via the second separator 220. In the recycle column 180, the at least portion of the compressed cracked olefin stream 172' and the liquid stream 164' may be separated in to the overhead vapor stream comprising $C_{5-}$ hydrocarbons in line 182' and the bottoms liquid stream comprising $C_{6+}$ hydrocarbons in line 186'.

The overhead vapor stream comprising $C_{5-}$ hydrocarbons in line 182' may be passed to the overhead receiver 190 of the recycle column 180 to provide the overhead receiver vapor stream in line 192' and the overhead receiver liquid stream 194'. The at least portion of the overhead vapor stream comprising $C_{5-}$ hydrocarbons in line 192b may be separated from the overhead receiver vapor stream 192' and recycled to the olefin cracking reactor 150. As shown, the at least portion of the overhead vapor stream comprising $C_{5-}$ hydrocarbons in line 192b may be combined with the hydrogenated effluent stream 112 from the hydrogenation reactor to form the combined stream 114 which is passed to the vaporizer 120. In an exemplary embodiment, the at least portion of the overhead vapor stream comprising $C_{5-}$ hydrocarbons in line 192b may be combined with the hydrogenated effluent stream 112 at a temperature from about 30° C. to about 50° C. The remaining portion of the overhead receiver vapor stream in line 192a may be passed to the first stage compressor 170 as described herein above. Rest of the process in same as described in FIG. 2.

The present scheme as shown in FIG. 3, is also suitable for the start-up and at turndown operations of the olefin cracking process while operating at lower than design feed and when the WHSV for the olefin cracking reactor 150 is low. Such periods of operation support unfavorable side reactions. Also, under such periods of operation the amount of $C_{6+}$ hydrocarbons available in the vapor form that can be obtained from the recycle column 180 is not significant for recycling. To improve an operating flexibility under such periods of operation, applicants have found that at least a portion of the overhead vapor stream comprising $C_{5-}$ hydrocarbons in line 192b and/or the depropanizer column bottoms stream comprising $C_{4+}$ hydrocarbons in line 244' may be recycled to the olefin cracking reactor 150 as described herein above to improve the light olefin yield of the olefin cracking process. Recycling the overhead vapor stream comprising $C_{5-}$ hydrocarbons in line 192b and/or the depropanizer column bottoms stream comprising $C_{4+}$ hydrocarbons in line 244' increases the reactor space velocity (WHSV) of the olefin cracking reactor 150. Which in turn favors light olefin yield and reduces heavies generation. A reduced heavies generation may also increase the amount of $C_{4+}$ material, particularly $C_4$-$C_6$ hydrocarbons, available for recycle from the depropanizer column bottoms.

Applicants have found that passing the overhead receiver vapor stream in line 192b, as shown in FIG. 3, to the vaporizer 120 minimizes any liquid carry over to the combined feed heat exchanger 130 and further equipment. Passing the overhead receiver vapor stream in line 192b at a temperature from about 30° C. to about 50° C. to the vaporizer 120 has various advantages. Firstly, passing the overhead receiver vapor stream at such temperatures facilitates the vaporization of the hydrogenated effluent stream 112 in the vaporizer 120 by lowering the vapor pressure within the vaporizer 120. Secondly, passing the vapor stream at such temperatures also reduces a dew point temperature of the recycle vapor stream thereby minimizing the amount of liquid that can condense in a recycle line when the recycle line is cool and not in use.

The current schemes of recycling the overhead vapor stream comprising $C_{5-}$ hydrocarbons, as shown in FIG. 2 and FIG. 3, boost the flow of feed to the olefin cracking reactor 150. Such schemes increase the WHSV of the olefin cracking reactor 150 to favor light olefins yield and reduces the over-cracking of the feed to the olefin cracking reactor 150. Also, recycling the overhead vapor stream comprising $C_{5-}$ hydrocarbons to the olefin cracking reactor 150, dilutes the olefinic concentration of the feed to an extent to impede oligomerization e.g. an olefin concentration of 50% or below. Accordingly, the present flow schemes of FIG. 2 and FIG. 3 may process a feed with high olefinic concentration greater than 90% which are prone to oligomerization under similar operating conditions.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect. Further, the figure shows one or more exemplary sensors such as 11, 12, 13, 21, 22, 23, 31, 32, and 33 located on or more conduits. Nevertheless, there may be sensors present on every stream so that the corresponding parameter(s) can be controlled accordingly.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

EMBODIMENTS

While the following is described in conjunction with specific embodiments, it will be understood that this description is intended to illustrate and not limit the scope of the preceding description and the appended claims.

A first embodiment of the invention is a process for cracking an olefinic feed comprising diolefins and monoolefins, the process comprising selectively hydrogenating the olefinic feed in a hydrogenation reactor to convert diolefins to monoolefins and provide a hydrogenated effluent stream; vaporizing the hydrogenated effluent stream in a vaporizer to provide a vaporized hydrogenated effluent stream; passing the vaporized hydrogenated effluent stream to an olefin cracking reactor to provide a cracked olefin stream comprising $C_2$ and $C_3$ olefins; passing the cracked olefin stream to a recycle column to provide one of an overhead vapor stream comprising $C_{5-}$ hydrocarbons or a side draw vapor stream comprising $C_{6+}$ hydrocarbons; and recycling at least a portion of the overhead vapor stream or the side draw vapor stream to the olefin cracking reactor. An embodiment of the invention is one, any or all of prior embodiments in this paragraph up through the first embodiment in this paragraph further comprising passing a remaining portion of the overhead vapor stream to a depropanizer column to provide $C_2$ and $C_3$ olefins. An embodiment of the invention is one, any or all of prior embodiments in this paragraph up through the first embodiment in this paragraph further comprising combining the at least portion of the overhead vapor stream or the side draw vapor stream with the vaporized hydrogenated effluent stream to provide a combined vaporized stream; and passing the combined vaporized stream to the olefin cracking reactor. An embodiment of the invention is one, any or all of prior embodiments in this paragraph up through the first embodiment in this paragraph further comprising passing the at least portion of the overhead vapor stream or the side draw vapor stream to the vaporizer along with the hydrogenated effluent stream. An embodiment of the invention is one, any or all of prior embodiments in this paragraph up through the first embodiment in this paragraph further comprising passing the cracked olefin stream comprising $C_2$ and $C_3$ olefins to a compressor to provide a compressed cracked olefin stream; and passing at least a portion of the compressed cracked olefin stream to the recycle column. An embodiment of the invention is one, any or all of prior embodiments in this paragraph up through the first embodiment in this paragraph further comprising passing a remaining portion of the compressed cracked olefin stream to the depropanizer column to provide $C_2$ and $C_3$ olefins. An embodiment of the invention is one, any or all of prior embodiments in this paragraph up through the first embodiment in this paragraph further comprising separating a bottoms liquid stream from the depropanizer column. An embodiment of the invention is one, any or all of prior embodiments in this paragraph up through the first embodiment in this paragraph, wherein the bottoms liquid stream comprises $C_{4+}$ hydrocarbons. An embodiment of the invention is one, any or all of prior embodiments in this paragraph up through the first embodiment in this paragraph, wherein the bottoms liquid stream comprises $C_{6+}$ hydrocarbons. An embodiment of the invention is one, any or all of prior embodiments in this paragraph up through the first embodiment in this paragraph further comprising recycling at least a portion of the bottoms liquid stream to the hydrogenation reactor at a combined feed ratio from about 11 to about 51. An embodiment of the invention is one, any or all of prior embodiments in this paragraph up through the first embodiment in this paragraph further comprising heating the vaporized hydrogenated effluent stream to a predetermined temperature prior to passing the vaporized hydrogenated effluent stream to the olefin cracking reactor. An embodiment of the invention is one, any or all of prior embodiments in this paragraph up through the first embodiment in this paragraph further comprising at least one of sensing at least one parameter of the process for cracking an olefinic feed comprising diolefins and monoolefins and generating a signal or data from the sensing; generating and transmitting a signal; or generating and transmitting data.

A second embodiment of the invention is a process for cracking an olefinic feed comprising diolefins and monoolefins, the process comprising selectively hydrogenating the olefinic feed in a hydrogenation reactor to convert diolefins to monoolefins and provide a hydrogenated effluent stream; vaporizing the hydrogenated effluent stream in a vaporizer to provide a vaporized hydrogenated effluent stream; passing the vaporized hydrogenated effluent stream to an olefin cracking reactor to provide a cracked olefin stream comprising $C_2$ and $C_3$ olefins; passing the cracked olefin stream to a recycle column to provide a first vapor stream comprising $C_{6+}$ hydrocarbons, and a second vapor stream comprising $C_{5-}$ hydrocarbons; and recycling the first vapor stream to the olefin cracking reactor; and passing the second vapor stream to a depropanizer column to provide $C_2$ and $C_3$ olefins. An embodiment of the invention is one, any or all of prior embodiments in this paragraph up through the second embodiment in this paragraph further comprising withdrawing the first vapor stream comprising $C_{6+}$ hydrocarbons as a side draw stream from the recycle column.

A third embodiment of the invention is a process for cracking an olefinic feed comprising diolefins and monoolefins, the process comprising selectively hydrogenating the olefinic feed in a hydrogenation reactor to convert diolefins to monoolefins and provide a hydrogenated effluent stream; vaporizing the hydrogenated effluent stream in a vaporizer to provide a vaporized hydrogenated effluent stream; passing the vaporized hydrogenated effluent stream to an olefin cracking reactor to provide a cracked olefin stream comprising $C_2$ and $C_3$ olefins; passing the cracked olefin stream to a recycle column to provide an overhead vapor stream comprising $C_{5-}$ hydrocarbons and a bottoms liquid stream comprising $C_{6+}$ hydrocarbons; and recycling at least a portion of the overhead vapor stream to the olefin cracking reactor. An embodiment of the invention is one, any or all of prior embodiments in this paragraph up through the third embodiment in this paragraph further comprising passing a remaining portion of the overhead vapor stream to a depropanizer column to provide $C_2$ and $C_3$ olefins. An embodiment of the invention is one, any or all of prior embodiments in this paragraph up through the third embodiment in this paragraph further comprising passing the overhead vapor stream to an overhead receiver of the recycle column to provide an overhead receiver vapor stream, and an overhead receiver liquid stream; combining at least portion of the overhead receiver vapor stream with the hydrogenated effluent stream; and passing at least a portion of the overhead receiver liquid stream and a remaining portion of the overhead receiver vapor stream to the depropanizer column to provide $C_2$ and $C_3$ olefins. An embodiment of the invention is one, any or all of prior embodiments in this paragraph up through the third embodiment in this paragraph further comprising passing the cracked olefin stream to a compressor to provide a compressed cracked olefin stream; passing at least a portion of the compressed cracked olefin stream to the recycle column; and passing a remaining portion of the compressed cracked olefin stream to the depropanizer column to provide $C_2$ and $C_3$ olefins. An embodiment of the invention is one, any or all of prior embodiments in this paragraph up through the third embodiment in this paragraph further comprising separating a bottoms liquid stream comprising $C_{4+}$ from the depropanizer column. An embodiment of the invention is one, any or all of prior embodiments in this paragraph up through the third embodiment in this paragraph further comprising recycling at least a portion of the bottoms liquid stream to the hydrogenation reactor at a combined feed ratio from about 11 to about 51.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for cracking an olefinic feed comprising diolefins and monoolefins, the process comprising:
   a) selectively hydrogenating the olefinic feed in a hydrogenation reactor to convert diolefins to monoolefins and provide a hydrogenated effluent stream;
   b) vaporizing the hydrogenated effluent stream in a vaporizer to provide a vaporized hydrogenated effluent stream;
   c) passing the vaporized hydrogenated effluent stream to an olefin cracking reactor to provide a cracked olefin stream comprising $C_2$ and $C_3$ olefins;
   d) passing the cracked olefin stream to a recycle column to provide an overhead vapor stream; wherein said overhead vapor stream comprises $C_{5-}$ hydrocarbons or said recycle column provides a side draw vapor stream comprising $C_{6+}$ hydrocarbons;
   e) passing a portion of the overhead vapor stream to a depropanizer column to provide $C_2$ and $C_3$ olefins; and
   f) recycling a remaining portion of the overhead vapor stream or the side draw vapor stream to the olefin cracking reactor.

2. The process of claim 1, wherein the recycling step comprises:
   combining the remaining portion of the overhead vapor stream or the side draw vapor stream with the vaporized hydrogenated effluent stream to provide a combined vaporized stream; and
   passing the combined vaporized stream to the olefin cracking reactor.

3. The process of claim 1, wherein the recycling step comprises passing the remaining portion of the overhead vapor stream or the side draw vapor stream to the vaporizer along with the hydrogenated effluent stream.

4. The process of claim 1 further comprising:
   passing the cracked olefin stream comprising $C_2$ and $C_3$ olefins to a compressor to provide a compressed cracked olefin stream; and
   passing at least a portion of the compressed cracked olefin stream to the recycle column.

5. The process of claim 4 further comprising passing a remaining portion of the compressed cracked olefin stream to the depropanizer column to provide $C_2$ and $C_3$ olefins.

6. The process of claim 1 further comprising separating a bottoms liquid stream from the depropanizer column.

7. The process of claim 6, wherein the bottoms liquid stream comprises $C_4+$ hydrocarbons.

8. The process of claim 6, wherein the bottoms liquid stream comprises $C_6+$ hydrocarbons.

9. The process of claim 6 further comprising recycling at least a portion of the bottoms liquid stream to the hydrogenation reactor at a combined feed ratio from about 1:1 to about 5:1.

10. The process of claim 1 further comprising heating the vaporized hydrogenated effluent stream to a predetermined temperature prior to passing the vaporized hydrogenated effluent stream to the olefin cracking reactor.

11. The process of claim 1 further comprising at least one of:
   sensing at least one parameter of the process for cracking an olefinic feed comprising diolefins and monoolefins and generating a signal or data from the sensing;
   generating and transmitting a signal; or
   generating and transmitting data.

12. A process for cracking an olefinic feed comprising diolefins and monoolefins, the process comprising:
   a) selectively hydrogenating the olefinic feed in a hydrogenation reactor to convert diolefins to monoolefins and provide a hydrogenated effluent stream;
   b) vaporizing the hydrogenated effluent stream in a vaporizer to provide a vaporized hydrogenated effluent stream;
   c) passing the vaporized hydrogenated effluent stream to an olefin cracking reactor to provide a cracked olefin stream comprising $C_2$ and $C_3$ olefins;
   d) passing the cracked olefin stream to a recycle column to provide a first vapor stream comprising $C_{6+}$ hydrocarbons, and a second vapor stream comprising $C_{5-}$ hydrocarbons; and
   e) recycling the first vapor stream to the olefin cracking reactor; and
   f) passing the second vapor stream to a depropanizer column to provide $C_2$ and $C_3$ olefins.

13. The process of claim 12 further comprising withdrawing the first vapor stream comprising $C_{6+}$ hydrocarbons as a side draw stream from the recycle column.

14. A process for cracking an olefinic feed comprising diolefins and monoolefins, the process comprising:
a) selectively hydrogenating the olefinic feed in a hydrogenation reactor to convert diolefins to monoolefins and provide a hydrogenated effluent stream;
b) vaporizing the hydrogenated effluent stream in a vaporizer to provide a vaporized hydrogenated effluent stream;
c) passing the vaporized hydrogenated effluent stream to an olefin cracking reactor to provide a cracked olefin stream comprising $C_2$ and $C_3$ olefins;
d) passing the cracked olefin stream to a recycle column to provide an overhead vapor stream comprising $C_{5-}$ hydrocarbons and a bottoms liquid stream comprising $C_{6+}$ hydrocarbons;
e) passing a portion of the overhead vapor stream to a depropanizer column to provide $C_2$ and $C_3$ olefins; and
f) recycling a remaining portion of the overhead vapor stream to the olefin cracking reactor.

15. The process of claim 14, wherein the recycling step comprises:
passing the overhead vapor stream to an overhead receiver of the recycle column to provide an overhead receiver vapor stream, and an overhead receiver liquid stream;
combining a portion of the overhead receiver vapor stream with the hydrogenated effluent stream; and
passing a portion of the overhead receiver liquid stream and a remaining portion of the overhead receiver vapor stream to the depropanizer column to provide $C_2$ and $C_3$ olefins.

16. The process of claim 14 further comprising:
passing the cracked olefin stream to a compressor to provide a compressed cracked olefin stream;
passing at least a portion of the compressed cracked olefin stream to the recycle column; and
passing a remaining portion of the compressed cracked olefin stream to the depropanizer column to provide $C_2$ and $C_3$ olefins.

17. The process of claim 14 further comprising separating a bottoms liquid stream comprising $C_{4+}$ from the depropanizer column.

18. The process of claim 17 further comprising recycling at least a portion of the bottoms liquid stream to the hydrogenation reactor at a combined feed ratio from about 1:1 to about 5:1.

* * * * *